United States Patent
Page

(10) Patent No.: US 6,214,362 B1
(45) Date of Patent: Apr. 10, 2001

(54) COSMETIC PAD FOR REMOVING LOW TENSION SUBSTANCES AND APPLYING COSMETICS

(76) Inventor: Darren L. Page, 6321 Mesa Cir., Stillwater, OK (US) 74074

(*) Notice: Subject to any disclaimer, the term of this patent is extended or adjusted under 35 U.S.C. 154(b) by 0 days.

(21) Appl. No.: 09/448,834

(22) Filed: Nov. 24, 1999

(51) Int. Cl.$^7$ .................................................. A01N 25/34
(52) U.S. Cl. .......................... 424/402; 424/401; 424/484
(58) Field of Search ................................ 424/70.1, 401, 424/484, 402, 482

(56) References Cited

U.S. PATENT DOCUMENTS

| | | | |
|---|---|---|---|
| 3,002,770 | 10/1961 | Chestnut | 285/94 |
| 3,315,020 | 4/1967 | Gore | 264/120 |
| 3,664,915 | 5/1972 | Gore | 161/164 |
| 3,953,566 | * 4/1976 | Gore | 264/288 |
| 4,277,429 | 7/1981 | Okita | 264/127 |
| 4,482,516 | 11/1984 | Bowman | 264/127 |
| 4,532,937 | 8/1985 | Miller | 128/759 |
| 4,643,939 | 2/1987 | Sugiyama | 428/283 |
| 4,917,134 | * 4/1990 | Simonzi | 132/320 |
| 4,981,145 | 1/1991 | Goldstein | 128/760 |
| 5,093,110 | * 3/1992 | Kamen et al. | 424/63 |
| 5,119,828 | 6/1992 | Miller | 128/760 |
| 5,512,277 | 4/1996 | Uemura | 424/78.03 |
| 5,689,364 | * 11/1997 | McGregor et al. | 359/350 |
| 5,935,521 | 8/1999 | Khazaka | 422/61 |

FOREIGN PATENT DOCUMENTS

WO99/36032 * 7/1999 (WO).

OTHER PUBLICATIONS

Shekarchi, I.c., Sever, J.L., Ward, L. 1982. Microsticks as solid–phase carriers for enzyme–linked immunosorbent assays. J. Clin. Microbiol., 16(6), 1012–18.*

Johnson & Johnson Clear touch™ Oil Absorbing sheets, copy of packaging description and instructions for use, ©J&J CCI 1999.

Bath & Body Works All–Natural Face Blotting Tissues, copy of packaging description and instructions for use.

Biomaterials Science and Engineering, by Joon Bu Park, Plenum Press, New York, pp. 80–84 ©1984.

* cited by examiner

Primary Examiner—Thurman K. Page
Assistant Examiner—Liliana Di Nola-Baron

(57) ABSTRACT

A multi-functional cosmetic pad (100) for either absorbing low tension substances from the skin or applying and smoothing new-makeup, comprising a porous low energy surface (110) and crease resisting features for preventing the formation of creases, folds, or kinks when the surface is rubbed over the skin. A cosmetic pad (100) in accordance with a preferred embodiment of the invention comprises a soft, conformable, and porous polytetrafluoroethylene membrane layered over a flexible backing (204). Flaps (308) cutout from a top portion (201) of the backing (204) form a retractable handle for easily gripping and manipulating the cosmetic pad (100).

10 Claims, 4 Drawing Sheets

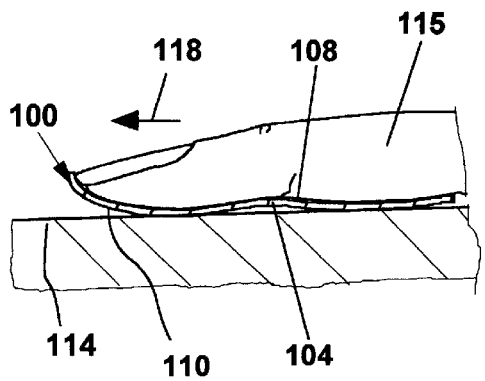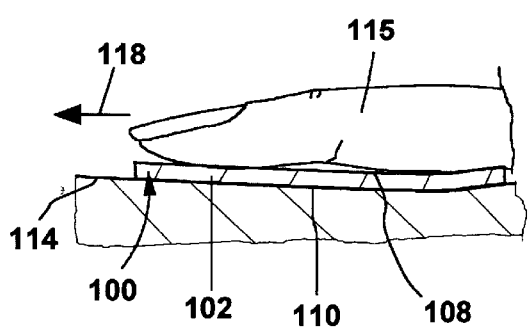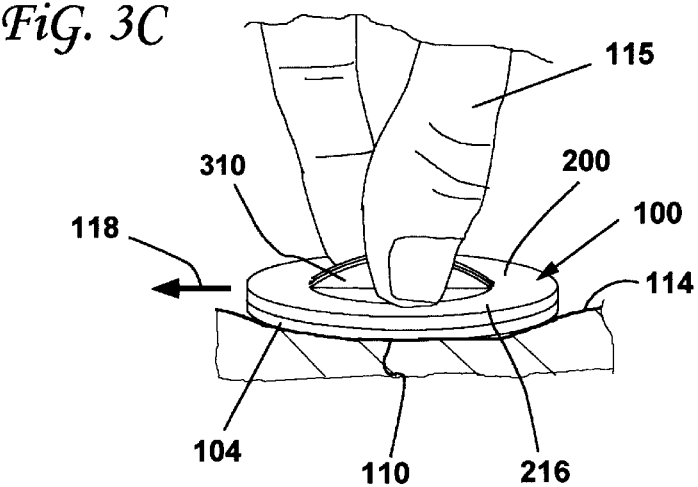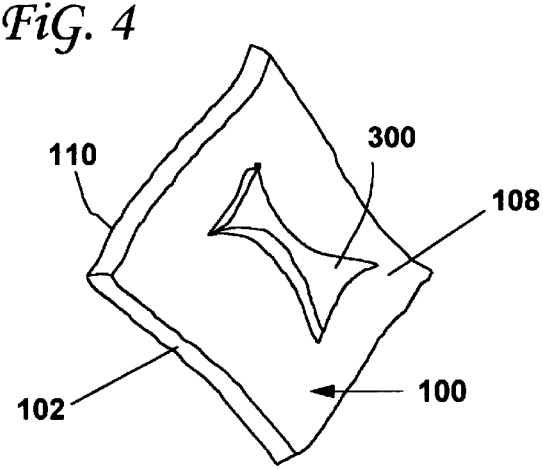

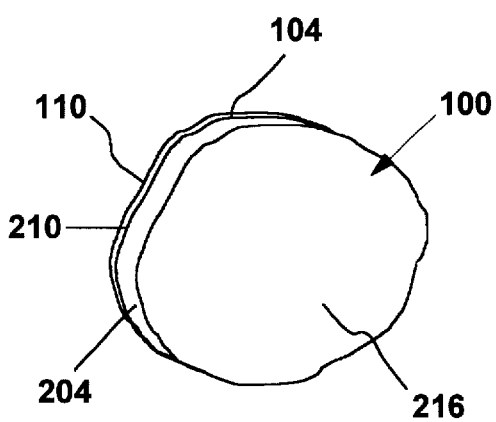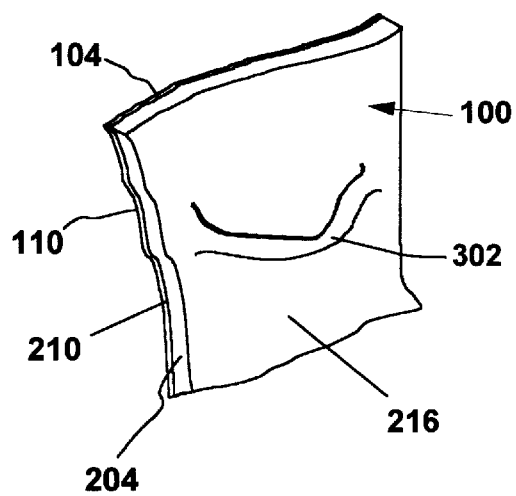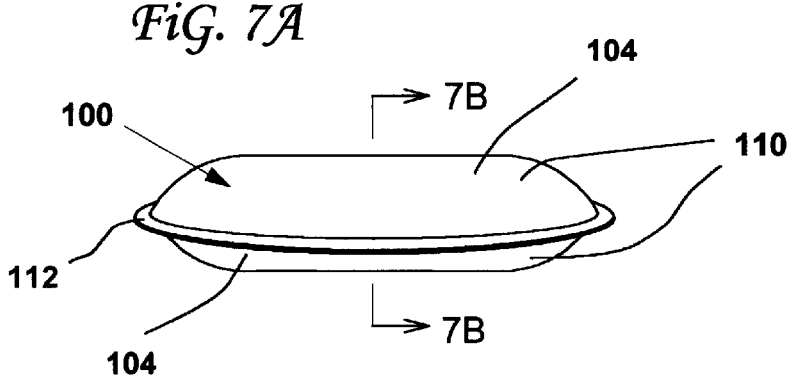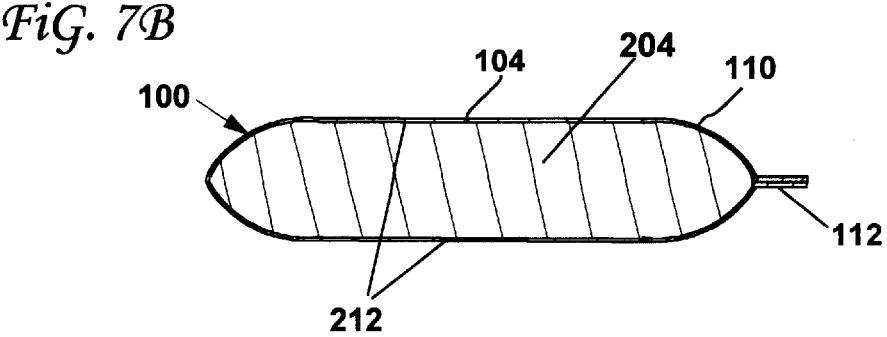

ns and blemishes, and specifically to cosmetic pads that are small, easy to hold and manipulate with the hand, and can be rubbed over the skin to remove oil without removing makeup. The cosmetic pads of the invention are also versatile and mutli-use as they can be further used to efficiently apply or smooth new-makeup, as well as, to remove sunscreen residues when no longer needed on the skin.

2. Discussion of Prior Art

Prior Art—Cosmetic Pads

The field of cosmetic pads is old and extensive. There exist many cosmetic pads commercially available for applying and/or removing makeup and for cleaning and/or wiping the skin. Makeup pads are commonly used to apply and remove makeup because bacteria and oil on the fingers may affect the skin health and/or the finish of the makeup foundation Makeup applicators and removal pads sold today are made of flexible porous materials. Some are made of natural cellulose fibers such as soft quilted cotton, hemp, or other natural plant fibers. These natural fiber cosmetic pads, such as the Cotton Rounds distributed by Albertson's Inc. Boise Id. 83726, are commonly found in grocery or drug stores. Other pads are made of synthetic polymer materials, e.g., low density polyethylene, latex, or similar sponge materials, such as Albertson's latex-free makeup Sponges, or the Beauty Rounds™ manufactured by Karlen Mfg., St Charles, Mich. 48655. Although effective for applying and removing makeup, these pads cannot remove oil without removing applied makeup. Therefore, if one attempts to clean the skin with these pads after application of makeup, the makeup will be removed by these pads. Further, although these pads are relatively effective at removing skin moisture and hydrophilic substances they are relatively ineffective at removing oil from the skin. When wiped or rubbed over the skin these relatively hydrophilic (i.e., moderate to high energy) materials will quickly absorb surface water and other polar compounds (e.g., makeup). The pre-absorption of high surface tension substances, like water, can also "lock-up" the pad to the subsequent absorption of low surface tension (hereafter low tension) substances (e.g., oils). The end result is that these pads will (a) dehydrate the skin by absorbing water moisture, (b) remove makeup, (c) not remove significant levels of oil, (d) will chafe or abrade the skin with repeated rubbing, and (e) waste relatively large amounts of makeup due to absorption into the pad when used to apply new-makeup. Further, those made of natural fibers tend to lose fibers onto the skin, which is unsightly in itself, and causes makeup to appear clumpy or otherwise coarse in texture.

Other available pads are fibrous pads or tissues saturated with astringents (Stridex®, Blistex Inc. Oak Brook, Ill. 60523) or skin cleaners (Ponds Cleaning & Make-Up Removal Towelette; Chesebrough-Ponds USA Co, Greenwich Conn. 06830). These pads are designed to remove oil and/or dirt or makeup from the skin and tighten the skin pores. These pads also remove large amounts of moisture and makeup with the oil they remove. Although the Stridex® pads have fairly coarse fibers, and tend not to lose fibers as readily as the softer tissues, they tend to be much more abrasive to the skin.

Consequently, although cosmetic pads of the prior art have been useful for removing and applying new-makeup, they have not been useful for both applying new-makeup and easily and quickly rubbing low tension substances, e.g., sebum skin oils, from the skin without removing makeup and necessitating its reapplication.

Prior Art—Skin Oil Absorbing Tissues and Sheets

Oil absorbing tissues and sheets have been proposed to remove skin oil from the skin and to indicate absorption of oil. Yasuo Sugiyama and Osamu Hiraoka (U.S. Pat. No. 4,643,939; issued on Feb. 17, 1987) teach an oil absorbing tissue, having an antibacterial compound, for preparing the skin prior to the addition of new makeup. The oil absorbing tissue, originally proposed in Japanese Examined Patent Publication (Kokoku) No. 56-8606, is described in the above Sugiyama et al. patent as teaching a cosmetic tissue comprised of a mixture of transparent synthetic resin fibers with nontransparent oil absorbing plant fibers. Portions of the tissue become transparent when oil is absorbed from the skin. Similar, all-natural oil absorbing "Face Blotting Tissues" (5.7 cm×8.3 cm (2¼"×3¼")) made of rice paper are manufactured for, and sold by Bath & Body Works, New Albany, Ohio 43054. The directions for use indicate to " . . . press one of our all-natural tissues gently against your face for a few seconds." When gently blotted onto the skin they will not smudge makeup. Although potentially more effective than conventional cosmetic pads at removing oil from the skin (and indicating the removal of oil), they have many disadvantages. First, these tissues comprise fibers that can absorb water moisture, absorb makeup, and abrade makeup from the skin. Further, the fibrous cellulose materials used have a relatively high friction coefficient with the skin, may abrade the skin with rubbing, and lose fibers affecting the appearance of the skin and subsequently applied makeup. Additionally, these tissues are relatively hard (Shore A hardness of 82) and stiff, and form abrasive creases and folds if rubbed over the skin, and are not useful for applying new-makeup.

Other oil absorbing sheets have been made of porous polymer materials. Johnson and Johnson Consumer Products Company (Division of Johnson and Johnson Consumer Companies, Inc. Skillman, N.J. 08558-9418) has marketed Clean and Clear® Clear Touch Oil™ Absorbing Sheets. These sheets are individual (5.4 cm×8.4 cm (2⅛" by 3⅝")), polymer sheets having physical and mechanical properties, and thickness dimensions similar to the hydrophobic polypropylene (PP) films taught in the oil monitoring and collection systems of Miller (U.S. Pat. Nos. 4,532,937 and 5,119,828, described in detail below). Differences include that the pore size of the sheets appear approximately 10× larger than the PP films described by Miller, they are colored blue, and are formed or machined with very small surface dimples or pits similar in shape to the dimples used in absorbent sheets, such as paper towels (likely to provide for more rapid oil absorption). The sheets are taught as rapidly soaking up oil and removing shine without smudging makeup or leaving behind powders or fibers. The directions for use are to: "Blot sheet gently on face to remove excess oil and shine". The absorption of oil is indicated by the material becoming more transparent to light and visually appearing a darker shade of blue. The hardness of the sheet, Shore A hardness of 85, and low conformability preclude them from being rubbed over the skin and they cannot be used to smoothly apply new-makeup. If rubbed over the skin they will form abrasive creases.

In sum, although the oil absorbing tissues and sheets of the prior art are effective for absorbing oil and not smudging makeup when blotted onto the skin, their use is very limited in that they cannot be rubbed over the skin and cannot be used to apply new-makeup. The relatively hard (i.e., Shore A Hardness greater than 81), stiff, and non-conforming mechanical properties of the materials utilized increase the pressure required for thoroughly removing oil from the skin, promote the formation of stiff creases, kinks, or folds, which feel rough against skin and will scrape makeup if rubbed over the skin. Further, the presence of a coarse fibrous structure or presence of surface dimples creates a textured surface that can scrape makeup if rubbed. Furthermore, because these sheets must be very thin, necessary to maintain some degree of flexibility in these relatively hard materials, they are difficult to hold, apply, and manipulate (especially for one person, such as a cosmetologist, to apply them to another person), and relatively large sheets are required to cleanse the entire human face of oil. The above listed features precluding the rubbing of the sheets of the prior art over the skin, also increase the difficulty and time required to effectively cleanse the entire human face of oil. Further, the surface energies of the materials of the prior art have been higher than ideal, imparting partial wetting of the sheets by water and makeup components, and therefore providing for the partial removal of makeup and skin moisture, especially at temperatures above 20° C. (e.g., skin temperatures) and under blotting pressures. Prior Art—Skin Oil Collection or Monitoring Systems Several oil collecting or absorbing devices have been proposed for collecting and monitoring the release of skin oil (sebum). U.S. Pat. No. 4,532,937 issued on Aug. 6, 1985, to David L. Miller, describes a "Sebum Collection and Monitoring Means and Method" comprising an open celled essentially hydrophobic polypropylene film having a high molecular weight pressure-sensitive adhesive on one side. The adhesive allows the film to be adhered to the skin until it becomes saturated, and thus turns transparent, from the locally produced sebum. The time duration required is relatively long, requiring from 5 up to 60 seconds. Prior to application the area of skin may be cleansed of oil using a solvent to remove surface sebum, such that sebum production can be monitored Although it is anticipated that these systems may be useful as treatments to remove skin sebum, presumably by a dermatologist, they are not useful for routine and simple cleansing of oil from the skin. Further, the adhesive used will remove makeup, leave a residue on the skin, and inhibit, by being placed between the skin and hydrophobic film, the absorption of oil into the membrane. Inhibition of absorption results in an increased time required to remove the oil under the patch. Further, one would have to have a large device to treat the entire human face, and would have to peel the first device off to apply a new one if more oil needed to be removed. Therefore, the features of the prior art preclude them from being rubbed over the skin.

The system of Miller (U.S. Pat. No. 4,532,937, described above) was subsequently modified to improve visualization. U.S. Pat. No. 5,119,828, issued on Jun. 9, 1992, to David L. Miller describes a porous hydrophobic film adhered to a paper board substrate material. The paper board material having a darkened area over which the film is applied, such that it is easier to tell when the film turns transparent upon the absorption of oil. The device is pressed against the skin for absorption of sebum and after some time period the device is removed from the skin. The sebum spot pattern may then be used for diagnostic purposes. This device cannot be applied as a cosmetic pad as taught herein because the relatively stiff and inflexible substrate, taught by Miller, precludes the rubbing of the membrane over the human face, as it would be very difficult to hold a pressure against the face while applying a force tangential to the surface (i.e., for rubbing the device around). Further, even if the substrate did not extend beyond the membrane as taught, the edges could scratch or cut the skin if the device was moved over the skin, especially over the contours of the human face.

Another sampling device and method for collection of sebum for the determination of a persons skin oil characteristics is taught in U.S. Pat. No. 4,981,145, issued on Jan. 1, 1991, to Jay A. Goldstein. The sebum absorbing portion is described as a thin porous paper sheet, such as cigarette paper, held next to the skin with a headband. The sheet's weight is known prior to application and if oil absorption is visually confirmed by the changes in light transmission, the paper is desiccated and weighed to determine the amount of oil absorbed and thus the amount of oil produced by the skin. The paper sheet utilized has a high surface energy and will readily wet with water, and hence the need for desiccation prior to weighing. Further, this sheet will readily absorb the relatively high surface tension compounds comprising makeup. Further, this porous sheet material tears easy, is relatively stiff, and does not conform well to the contours of the human face, precluding its rubbing over the skin.

Another measuring system for determining the secretion of sebum from the skin is taught by Khazaka (U.S. Pat. No. 5,935,521, issued on Aug. 10, 1999). Khazaka teaches a microporous water-repellent, sebum-absorbing opaque foil having its edges secured to an annular substrate film. The system is placed against the skin to absorb sebum oils and absorption is indicated by the foil turning transparent The foil is made of porous PP similar to that used by Miller. The substrate film is constructed of a rigid material having enough flexibility to allow the system to be pressed against the skin without kinking of the foil. Although potentially easier to apply to the skin and providing optoelectronic measurement capabilities, the system is not useful for quickly removing low surface tension substances from the skin without removing makeup and for applying new-makeup. The system of Khazaka avoids using the paper board backing, which significantly increases the rigidity of the membrane, taught by Miller. However, the area supported by the substrate will have significantly increased rigidity and inflexibility. Further, the annular support produces an outer edge and inner edge (where the foil extends beyond the support) that would be abrasive if rubbed over the skin. Further these supports are very thin, making them difficult to grasp especially in a manner to facilitate rubbing. The PP foils taught are relatively rigid, Shore A hardness >75, and inflexible themselves and will not conform well to the contours of the skin, and will form creases if rubbed over the skin.

In sum, although effective for collecting and monitoring the production rate of local skin sebum these prior art devices and methods cannot be used to provide the features and uses of my cosmetic pad. The sebum collecting and monitoring systems have required relatively thin porous sheets and long time periods, insuring that the entire sheet thickness will be saturated with, and thus indicate, the oil arising from a selected skin portion. The oil indicating principle is dependent on the saturation of the membrane pore volume to induce a change in the light transmission properties of the membrane. Consequently, the great advantages of the present invention including the removal of sebum from a large area of skin, e.g., the entire face, and by rubbing over the skin are foreign to the teachings of the prior art. My cosmetic pad does not require local securing (i.e., by manual pressing, an adhesive, or securing via a headband) to a local area until a visible change in light transmission occurs, and is not limited to light blotting or pressing onto the skin.

Prior Art—Oil Absorbing Particulate Additives

Several compositions, e.g., makeup compositions, incorporating oil absorbing powders have been described. Although these compositions can effectively maintain a "shine-free" appearance to the skin for a longer duration, than without, the addition of oil absorbing powders in significant amounts can give the skin a gritty or textured appearance. Therefore, the amounts typically added to makeup compositions will typically saturate before desired. The user then ends up with a layer of oil saturated particulates stuck to the skin. The particulates must then be removed from the skin in order to remove the absorbed oil. My cosmetic pad is useful for the removal of these oil saturated powders.

SUMMARY OF THE INVENTION

Those in the art have appreciated that porous low surface energy (hereafter low energy) "hydrophobic", sheets will absorb oils from the skin and that these sheets will become more transparent to light when oil is absorbed. Further, those in the art have appreciated that these sheets may be blotted onto the skin without smudging makeup or leaving behind powder. However, heretofore, the skin oil absorbing sheets, tissues, and devices have been relatively large, difficult to manipulate with the hand, and cannot be readily rubbed over the skin without abrading the skin, forming abrasive creases, kinks or ridges, and/or removing previously applied makeup. Further, the oil absorbing sheets and systems of the prior art have been inefficient at drying the skin of oil, have not been useful for also applying and smoothing new-makeup onto the skin, and have been very difficult for cosmetologists or dermatologists to apply to a client's skin without bunching or dropping. Consequently, my cosmetic pad has great advantages that have not been appreciated, recognized, or attained by the prior art.

The Applicant has discovered features providing for low tension substance absorbing cosmetic pads that resist the formation of folds, creases, ridges or kinks (hereafter creases) when rubbed or wiped over the skin. Additionally, the unique features of the cosmetic pad taught herein provide for a cosmetic pad having improved low tension substance removal, having reduced dimensions, that are more easily held and manipulated, that are less abrasive to the skin, and having multi-functionality in that they can also be used to apply new-makeup.

Further, my cosmetic pad will significantly remove the "water proofing" compounds utilized in sunscreens, even if the skin is wet or moist with water. Although these water-resistant formulations are touted as skin friendly, they can promote skin blemishes by plugging pores, effecting the gas permeability of the skin, and hindering natural release of water that occurs during sweating. It is therefore advantageous to remove these compounds when the sun's rays are no longer a threat, in order to prevent the formation of skin blemishes. This is another advantage that has not been appreciated or recognized and allows users to improve the appearance and health of the skin when the presence of sunscreen is no longer needed.

OBJECTS AND ADVANTAGES

Accordingly, besides the objects and advantages of my cosmetic pads described in my above patent, several objects and advantages of the present invention are:
(a) to provide a cosmetic pad that will resist the formation of abrasive creases when rubbed over the skin
(b) to provide a cosmetic pad that will absorb low tension substances from the skin
(c) to provide a cosmetic pad that can be rubbed against the skin to remove skin oil without removing, smudging, or otherwise adversely effecting the appearance of makeup
(d) to provide a cosmetic pad that can be easily gripped and manipulated for rubbing over the skin
(e) to provide a cosmetic pad that can be easily applied by one person, such as a cosmetologist, to another person
(f) to provide a cosmetic pad that can also be used to apply and smooth new-makeup and reduce the amount of new-makeup wasted by soaking into the pad
(g) to provide a cosmetic pad that is conformable to the contours of face and microtextures of the skin
(h) to provide a cosmetic pad that will thoroughly clean oil from the skin with light urging
(i) to provide a cosmetic pad that can cleanse a large skin area, e.g., the entire human face, of low tension substances
(j) to provide a cosmetic pad that will not remove water moisture from the skin
(k) to provide a cosmetic pad that will not lose fibers or particles onto the skin and therefore not cause makeup to appear clumpy or coarse
(l) to provide a cosmetic pad that will not chafe or abrade the skin with repeated rubbing or application
(m) to provide a cosmetic pad that is nontoxic and hypoallergenic to the skin
(n) to provide a cosmetic pad that can be used to remove pore clogging compounds found in water resistant sunscreens Further objects and advantages are to provide cosmetic pads that can be colored, sterilized, packaged individually or in tear-off-links. Additional objects and advantages are to provide cosmetic pads that are simple to use, inexpensive to manufacture, disposable, and portable. Still further objects and advantages will become apparent from considering the ensuing description and drawings.

BRIEF DESCRIPTION OF THE DRAWINGS

Drawing FIGS. 1 to 9C

In the drawings, closely related figures have the same number but different alphabetic suffix.

FIG. 3A is a sectional view illustrating the crease resisting features of one preferred thin membrane embodiment of the cosmetic pad of the present invention.

FIG. 3B is a partial sectional view illustrating the crease resisting features of the thick membrane cosmetic pad embodiment of the present invention, previously shown in FIG. 1.

FIG. 3C is a partial sectional view illustrating the crease resisting features of a cosmetic pad of the present invention having a substantially thin membrane layered over a flexible backing.(this embodiment is shown in more detail in FIGS. 9A–9C)

FIG. 4 is a perspective view of a substantially thick membrane cosmetic pad in accordance with one embodiment of the invention and including a handle for easier manipulation.

FIG. 5 is a perspective view of a disc shaped cosmetic pad in one embodiment of the present invention comprised of a substantially thin membrane layered onto one face of a flexible backing FIG. 6 is a perspective view of a rectangular shaped cosmetic pad in one embodiment of the present invention comprised of a substantially thin membrane laminated onto one face of a flexible backing and including a handle strap for easier manipulation of the cosmetic pad FIG. 7A is a perspective side view of a disc shaped cosmetic pad in another embodiment of the present invention comprising a flexible backing encapsulated by a substantially thin membrane.

FIG. 7B is a sectional view of the cosmetic pad of FIG. 7A illustrating the encapsulation of the backing by the thin membrane.

DESCRIPTION OF INVENTION

FIGS. 1 to 9C

Figure 1:
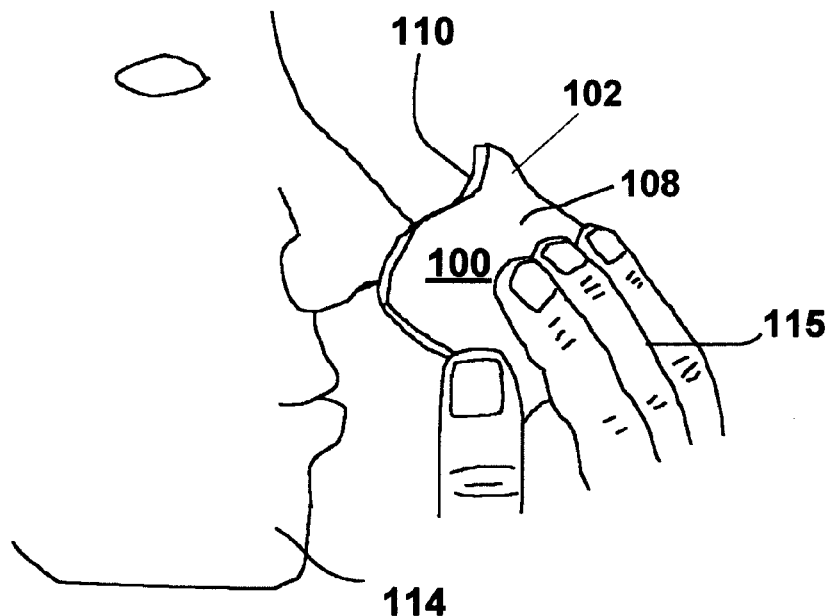
FIG. 1 is a perspective view of a cosmetic pad comprising a substantially thick membrane in accordance with a preferred embodiment of the present invention.

There is a greatly underappreciated and overlooked need for efficient, preferentially oil absorbing, cosmetic pads that can be easily held and rubbed over the skin. My cosmetic pad allows, for the first time, one to easily treat the skin by removing blemish causing oils, and refresh the appearance of makeup throughout the entire day without removing pre-applied makeup and necessitating its reapplication. Further, my cosmetic pad allows for the first time the easy removal of low tension substances from the skin of one person by a second person, such as a cosmetologist. Additionally, my cosmetic pad is efficient at applying and smoothing new-makeup onto the skin. This is a great advantage over the prior art, as a user is not required to carry or purchase several different pad types to perform daily makeup maintenance. Further, when used to apply new-makeup, my cosmetic pad also wastes much less new-makeup due to absorption into the pad. Because makeup can be very expensive, this significant reduction in wasted makeup can save individual users and cosmetologists significant amounts of money.

The Applicant has discovered that the relatively unappreciated and unsolved need for small, easily manipulated cosmetic pads useful for both thoroughly rubbing low tension substances from the skin, without removing makeup, and applying new-makeup to the skin, can be accomplished by constructing cosmetic pads having features, including unique physical properties, providing resistance to the formation of wrinkles, creases, kinks, and ridges (hereafter creases) in the low energy surface of the cosmetic pad, when rubbed over the skin. The Applicant has discovered that the formation of creases may be precluded by either (I) employing a substantially thin (preferably less than about 0.8 mm (30 mil), more preferably less than about 0.4 mm (15 mil), and most preferably less than about 0.13 mm (5 mil) membrane composed of a low energy material having a high degree of softness and high degree of conformability, such that the membrane can be urged to tightly conform and adhere to the fingers, e.g., when plastically deformed over a finger; (II) employing a substantially thick (preferably greater than about 0.3 mm (10 mil), more preferably greater than about 0.5 mm (20 mil), and most preferably greater than about 0.6 mm (25 mil) membrane having preselected physical properties including a high level of softness and conformability, such that the membrane will not substantially adhere to the hand and will not form creases when rubbed over the skin; or (III) layering a low energy membrane (preferably less than about 2.5 mm (100 mil), more preferably less than 0.8 mm (30 mil), and most preferably less than 0.4 mm (15 mil), having preselected physical properties, including a high softness and high conformability, over a soft flexible backing material.

The preferred conformability and softness properties of the low energy membrane are dependent on the crease resistant features employed. For crease resisting features (I) and (II), the conformability should be greater than about 7%, preferably greater than about 9%, and most preferably greater than about 12%, and the softness, as indicated by a Shore A Hardness, should preferably be less than about 75, more preferably less than about 60, and most preferably less than about 50. For crease resisting features (III), the conformability should be greater than approximately 5%, preferably greater than about 7%, and most preferably greater than about 9%, and the softness, as indicated by the Shore A Hardness, should be preferably less than about 90, more preferably less than about 70, and most preferably less than approximately 60. The use of a soft flexible backing allows the preferred conformability and softness properties to be relaxed because of the tangential support provided by the backing.

Shore A hardness values are determined according to ASTM D 2240. Thin membranes are built up to 6 mm (¼") thickness for testing. The conformability is determined by measuring the conformability of a thin (approximately 0.08 mm (3 mil)) sheet or tape of the material to a highly textured surface, under a given force, as taught by W. L Gore in U.S. Pat. No. 3,664,915 issued on May 23, 1972. Conformability values for non-expanded and expanded PTFE membrane materials are given in Gore (U.S. Pat. No. 3,664,915).

Low tension substances that can be preferentially removed by my cosmetic pad are substances having a surface tension preferably less than about 50 Dynes/cm, more preferably less than about 40 Dynes/cm, and most preferably less than about 30 Dynes/cm. For reference, water has a surface tension of 72.75 Dynes/cm and n-hexane has a surface tension of 18.43 Dynes/cm. In practice, low tension substances that can be preferentially removed from the skin with my cosmetic pads include the skin oils (e.g., squalene, wax esters, triglycerides, and fatty acids), and the low tension ingredients of sunscreens (e.g., oil emollients, surfactants or emulsifiers, thickeners, and fatty acids).

The low energy membrane materials useful for implementing this invention should preferably have a contact angle (θ) with water greater than 70°, more preferably greater than 90°, and most preferably greater than 100°. Contact angle measurements and surface tension data herein are given for a reference temperature of 20° C., unless otherwise noted. The contact angle of water with the material gives an indication of the wetting of the material by applied water and the relative surface energy level of the material. Although the wetting characteristics are approximately a linear gradient with regard to the contact angle, in regard to this teaching, they can be generalized as follows: (a) θ<20° indicates complete wetting by water and a very high surface energy material, (b) $20° \leq θ < 60°$ indicates substantial wetting by water and a high surface energy material, (c) $60° \leq θ < 80°$ indicates partial wetting by water and a moderate surface energy material, (d) $80° \leq θ < 90°$ indicates substantial non-wetting by water and a low surface energy material, and (e) θ>90° indicates nonwetting by water and a very low energy material. The contact angle of water with a material is a well known property determined by placing a drop of water on the material at 20° C. and measuring the equilibrium angle formed between the drop and the material. A more detailed description of this technique can be found in Biomaterials Science and Engineering by Joon Bu Park, Plenum Press, New York (1984), pp. 80–84.

The water contact angle of the membrane surface is important because it gives a measure of how well water and water soluble compounds, such as makeup, will resist wetting and absorbing into the membrane. Wetting of the membrane by water can "lock-up" the membrane to subsequent absorption of low tension oils and significantly enhance the absorption of polar water soluble compounds, such as those comprising oil-free makeups. A non-wetting measurement for water indicates significant resistance to wetting of the membrane by the moderate and high surface tension compounds comprising oil-free makeups, such as propylene glycol. For constructing my multi-use pad having low tension substance absorbing utility, the membrane surface should be porous. The pore size of the surface material is a factor effecting the rate of low tension substance absorption. For substantially instantaneous absorption, the mean pore size of the membrane surface should be preferably between about 0.01 μm and 500 μm, more preferably between about 0.05 μm and 200 μm, and most preferably between about 0.1 μm and 100 μm. Importantly, when a cosmetic pad having only makeup saving utility is desired, porosity is not required.

The most preferred material for forming the low energy, soft, and conformable surface of my cosmetic pad is polytetrafluoroethylene (PTFE). Examples of useful PTFE materials include the non-expanded tapes or ribbons taught in (a) U.S. Pat No. 2,002,770, issued on Oct. 3, 1961, to J. A. Chestnut, and (b) U.S. Pat. No. 3,315,020, issued on Apr. 18, 1967, to W. L. Gore. Further examples are the porous PTFE membranes including (a) the expanded tapes taught in U.S. Pat No. 3,664,915 issued on May 23, 1972, to W. L. Gore, (b) the porous PTFE products taught in U.S. Pat No. 3,953,566, issued on Apr. 27, 1976, to R. W. Gore, (c) the Asymmetric porous PTFE taught in U.S. Pat. No. 4,277,429, issued on Jul. 7, 1981, to K. Okita, (d) and the coarse microstructure membranes taught in U.S. Pat. No. 4,482,516, issued on Nov. 13, 1984, to Bowman et al. These teachings are hereby incorporated by reference. The desirable properties of these PTFE materials include a very low energy (contact angle between water and PTFE of about 108°), a high conformability (typically 5% to greater than 25%), a high level of softness (Shore A hardness typically less than about 50), a very low coefficient of friction with skin relative to porosity, the capacity for porosity, and the capacity for a very high degree of porosity (to greater than 90%).

The non-expanded, and generally considered non-porous, PTFE membrane materials, e.g., as taught by Chestnut (U.S. Pat. No. 2,002,770) and Gore (U.S. Pat. No. 3,315,020), can be used to construct makeup saving makeup applicators, as is, or rendered porous and thus absorptive by stretching the material at room temperature. Porosity does not substantially effect the affinity of the membrane for the low tension substances but can very substantially increase the surface area of the membrane available for binding and absorbing these low tension substances. For example, stretching the PTFE material, taught by Chestnut (U.S. Pat. No. 2,002,770), to elongations of about 1.1 times the original dimensions, or greater, can increase the low tension substance absorption by approximately 10 to greater than 1000 fold. The stretching of the material opens up the microscopic fiber and node structure of the material, increasing pore size and porosity and thereby allowing infiltration of the low tension substances.

Although prior stretching is not required when using porous PTFE materials, it has been discovered by the Applicant that post manufacture stretching will also significantly enhance the absorption rate of low tension substances by porous PTFE materials. This is essentially dependent on surface pore size, as pore sizes greater than about 0.1 μm are more effective at allowing fast infiltration of low tension substances into the PTFE matrix. Therefore, stretching at room temperature can be used to increase surface pore size of an expanded PIFE membrane and "break" any tight pored skin that may have formed during manufacture of the membrane. Consequently, prior stretching of the expanded PTFE membranes has been found by the Applicant to substantially increase the rate of absorption of low tension substances. For example, improved absorption of low surface tension substances by the expanded PTFE tapes, e.g., those taught by Gore (U.S. Pat. No. 3,953,566), can be accomplished by stretching to 1.1 or greater elongations in the lateral, non-machine, direction. In lieu of post manufacture stretching, appropriate steps may be taken in the manufacturing process to insure a more preferred surface pore size and/or prevent the formation of a tight-pored skin on the surface of the membrane. Referring to the drawings, a Cosmetic pad 100 in accordance with a preferred embodiment of the invention, is illustrated in FIG. 1. Cosmetic Pad 100 is comprised of a substantially thick membrane 102 made of a soft, conformable, and low energy material and having a back side 108 and a porous surface 110. In use, the pad is held by fingers 115 and surface 110 is contacted to skin 114 and rubbed over skin 114 to remove low tension substances or to apply new-makeup. The soft and conformable nature of the porous membrane make the pad easy to hold, provides a grip to the hand and fingers and allows the pad to have a thickness insuring crease resistance while still maintaining flexibility.

Figure 2:
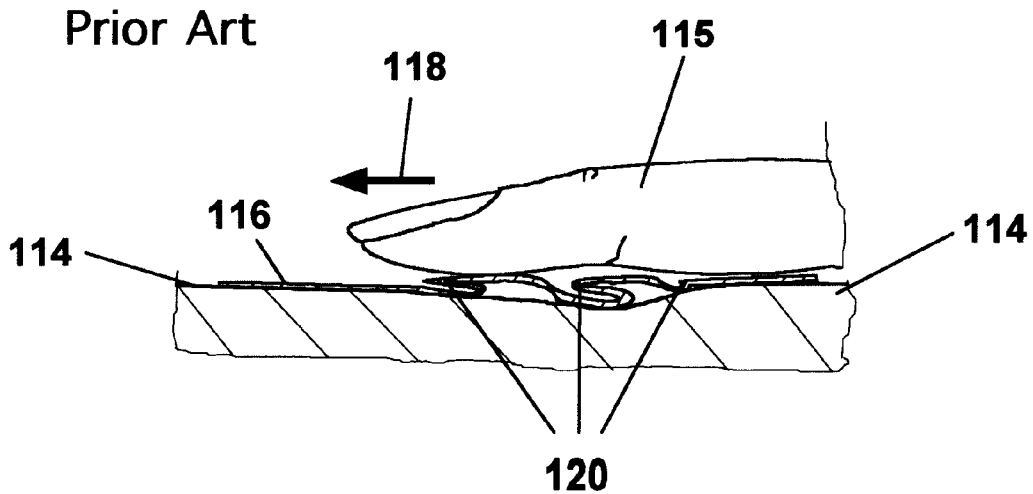
FIG. 2 is a partial sectional view of the oil absorbing sheets of the prior art and illustrating the disadvantages and limitations of the prior art if rubbed over the skin.

A major disadvantage of the oil absorbing sheets of the prior art is illustrated in FIG. 2. The oil absorbing sheets of the prior art are restricted to blotting onto the face because the materials used to form the sheets are relatively hard, nonconformable, stiff and inflexible, and abrasive. Consequently, when a prior art oil absorbing sheet 116 is rubbed (exemplified direction indicated by arrow 118) over skin 114, prior art sheet 116 will form creases, kinks, or folds 120 that inhibit the effective removal of skin oil, scrape and/or smudge makeup from the skin, abrade the skin, and would prevent the even application of new-makeup. As such, the directions for use on the packaging of the oil absorbing sheets of the prior art indicate that they should be lightly blotted onto the skin to remove oil.

The features of my cosmetic pad providing for resistance to the formation of creases when rubbed over the skin are illustrated in FIGS. 3A, 3B, and 3C. Arrows 118 indicate the exemplified direction of rubbing motion in these figures.

FIG. 3A illustrates that the formation of creases in my cosmetic pad 100 embodiment comprised of thin membrane 104, is precluded by using materials having preselected softness, and conformability, and thickness, such that the thin membrane cosmetic pad 100 can be urged to tightly conform and adhere to the hand or finger 115. Thin membrane 104 conforms and adheres to finger 115 so that when its oil absorbing porous surface 110 is rubbed over skin 114 it will not form creases. The adhesion of thin membrane cosmetic pad 100 to finger 115 may also be enhanced using a tacky adhesive, like that used on Post-It™ notes, pre-applied to back side 108. Further advantages of this embodiment include that cosmetic pad 100 can be used without touching porous surface 110 with the fingers.

FIG. 3B illustrates that the preselected softness and conformability properties of the materials taught in the invention also allow the prevention of creases when tight conformation of cosmetic pad 100 with finger 115 is not desired. By employing a substantially thick, soft, conformable membrane 102, cosmetic pad 100 will resist the formation of creases when porous surface 110 is rubbed over skin 114. The selected properties of the membrane material allow significant thicknesses to the membrane while maintaining a high degree of flexibility and overall conformability to cosmetic pad 100. The gripping of membrane 102 may be enhanced by texturing back side 108 of membrane 102. The backside may be textured by applying a pattern of silicone glue material. The embodiment shown in FIG. 3B is the same embodiment as shown in FIG. 1.

FIG. 3C illustrates that resistance to the formation of creases may also be implemented in the construction of my cosmetic pad 100, comprising a relatively thin membrane 104, by layering membrane 104 over flexible backing 200. This embodiment does not require close conformation and adhesion to finger 115 and minimizes the volume of membrane material used. Additionally, the ease of holding and rubbing cosmetic pad 100 over skin 114 is improved by including collapsible finger handle or grip 310. The embodiment of FIG. 3C is illustrated in more detail in FIGS. 9A, 9B, and 9C.

Referring to FIG. 4, the ease of manipulating the thick membrane embodiment shown in FIG. 1 and FIG. 3B, may also be enhanced by a finger handle 300 disposed on back side 108 of membrane 102. Handle 300 may be made of the same material as membrane 102 or may be made of an inexpensive alternate material such as cotton or sponge.

When adhesion to the fingers is not desirable, a thin inexpensive membrane can still be used when layered over a soft and flexible backing. Disc shaped cosmetic pad 100 made in accordance with an embodiment of the present invention having a thin membrane 104 laminated over a face 210 of backing 204, is shown in FIG. 5. Membrane 104 provides low energy and porous surface 110 for contacting the skin. Backing 204, having top side 216 is most preferably made of a porous high or moderate surface energy material, such as those commonly utilized to make cosmetic pads of the prior art, e.g., the low density polyethylene, polypropylene, or latex sponge materials, or the cotton, hemp, or other natural plant fiber materials. Less membrane is required when a high energy backing is included because a significant amount of the low tension substance will be transferred to the backing, thereby freeing up the membrane to absorb more low tension substances from the skin.

FIG. 6 shows a rectangular shaped cosmetic pad 100 made in accordance with another embodiment of the present invention comprising thin membrane 104 laminated over face 210 of backing 204, and further including finger strap or handle 302, disposed on top side 216, for easily handling cosmetic pad 100 without touching surface 110 with the fingers.

Lamination may be performed using an adhesive. Many adhesives can be used to bond porous low energy materials, such as stretched or expanded PTFE, because the adhesive can infiltrate the pores and bond into the microscopic structures of the material, e.g., the fiber and node structure of the expanded PTFE materials. Consequently, many adhesives can be used to bond porous low energy membranes to backing materials, and the adhesive can be selected based on desired attributes, such as quick drying, high flexibility, or cost For example, membranes may be secured to backing materials using a fast drying adhesive such as the cyanoacrylate or similar adhesives commonly sold as super-glues (e.g., Bondini®-2 glue from Pro-Tel, Inc, Santa Monica, Calif. 90401)

However, referring to FIG. 5 and FIG. 6, when thin membrane 104 is to be layered by lamination directly to backing 204, the preferred method of lamination should not fill the pores of surface 110, and should not hamper transfer of low tension substances from thin membrane 104 to backing 204. Preferred lamination may be accomplished using a solvent adhesive (e.g., perfluorinated alkanes and cycloalkanes, such as, perfluoro (tetradecahydrophenanthrene) that can bond expanded PTFE without significantly penetrating the pores. Other bonding methods useful for maintaining porosity of the surface include ultrasonic or heat welding, applying an adhesive in the form of a discontinuous porous coating, and insert molding (e.g., a porous membrane may be applied to a polymer foam backing material before the foam is solidified and then cut into the desired shape and size). Maintaining the capacity for transfer of low energy substances from the membrane to the backing material allows much higher volumes of low tension substances to be removed than without the backing present and reduces the thickness of the membrane required to cleanse a given area of skin.

My cosmetic pad may also be constructed having multiple surfaces for absorbing low tension substances or for applicating new-makeup. FIG. 7A and FIG. 7B show a multiple active surfaced cosmetic pad 100 comprised of thin membrane 104 encapsulating a backing material. Referring to FIG. 7B, backing 204 has a continuous face 212. Seam 112 may be formed by adhesive or by heat sealing. Backing 204 may be disc shaped, rectangular, or spherical (such as a cotton ball). Further, the soft and conformable membrane 104 can be plastically deformed around backing 204 such that only a very small seam or overlapping region of the membrane is exhibited.

Figure 8A:
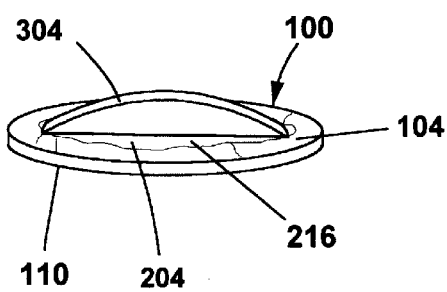
FIG. 8A is a perspective view of a cosmetic pad of a preferred embodiment of the present invention comprised of a substantially thin membrane layered, over one face and the edges of, a disc shaped backing material and also including a finger handle for easier manipulation.
Figure 8B:
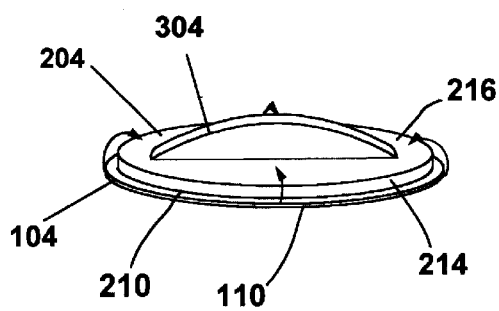
FIG. 8B is a perspective view illustrating the construction of the cosmetic pad of FIG. 8A.

FIG. 8A shows a cosmetic pad in accordance with an embodiment of the present invention comprising thin membrane 104 layered over disc shaped backing 204. The construction of cosmetic pad 100 of FIG. 8A is exemplified in FIG. 8B. Referring to FIG. 8B, membrane 104 is layered, by conforming (indicated by arrows) over face 210 and edge face 214, onto backing 204, and adhered to top side 216 of backing 204 such that there exists no potentially abrasive edge. Additionally, lamination is completely avoided between membrane 104 and face 210 and edge face 214, so as to maintain the softness, flexibility, or porosity of surface 110. Cosmetic pad 100 of FIGS. 8A and 8B also includes finger handle or grip 304 for easily handling cosmetic pad 100 Finger handle 304 may be adhered to top side 216 of backing 204 using an adhesive or formed as a part of backing 204.

Figure 9A:
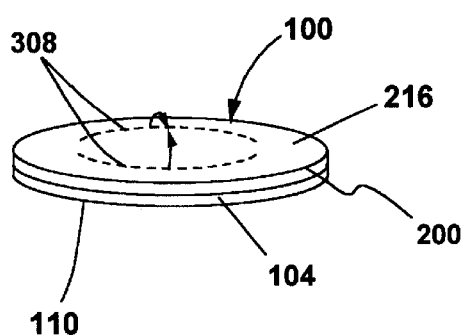
FIG. 9A is a perspective view of a cosmetic pad of a preferred embodiment of the present invention having a backing comprised of two portions for improving the top appearance of the cosmetic pad and providing for a collapsible finger handle.
Figure 9B:
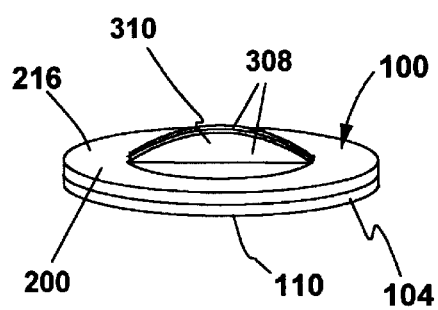
FIG. 9B is a perspective view of the cosmetic pad of FIG. 9A, showing the collapsible finger handle in the upright position for use.
Figure 9C:
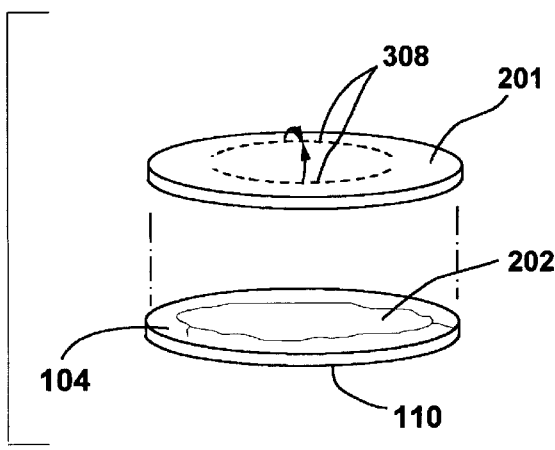
FIG. 9C is a perspective exploded view illustrating the construction of the cosmetic pad of FIGS. 9A and 9B.

FIGS. 9A, 9B, and 9C illustrate a cosmetic pad in accordance with another embodiment of the present invention having no visible adhesion area and having collapsible finger handle 310 for reducing material used and allowing more compact storage and packaging. FIG. 9A shows cosmetic pad 100 comprising thin membrane 104 layered over a face of backing 200. Referring to FIG. 9C, backing 200 is comprised of a top portion 201 and a bottom portion 202. A collapsible fingerhandle 310 (shown in raised position in FIG. 9B) is formed from flaps 308 cutout from top portion 201. Referring to FIG. 9C, the seamless design is produced by first layering thin membrane 104 onto bottom portion 202 of backing 200, in a manner analogous to the embodiment shown in Fig 5B, and then laminating backing portion 201 to portion 202. Alternately, top portion 201 may be made of a loose material such as cotton such that it will form a finger handle when pinched between the fingers.

Operation

FIGS. 1, 3 to 9C

The manner for using my cosmetic pads is similar to the cosmetic makeup pads in present use. Specifically surface 110 of the pad is rubbed or wiped over the skin Commonly, roughly circular motions are employed to remove substances from selected areas or to smooth out or apply new-makeup. When used to apply new-makeup, makeup is typically first applied to surface 110 and then rubbed over skin 114.

The method of gripping my cosmetic pads is dependent on the embodiment Cosmetic pad 100 of FIG. 1 and 3B having a thick membrane 102, and cosmetic pad 100 of FIGS. 5 and 7, having a membrane 104 layered over backing 204, and not having a handle, are gripped analogous to the cosmetic pads in present use, i.e., the pad can be gripped with the fingers on the back of the pad and with the thumb catching the edge. However, my cosmetic pad embodiments having a handle (referring to FIGS. 3C, 4, 6, 8A–B and 9A–C) are gripped by gasping handle 310, 300, 302, 304, and 310, respectively, with the fingers thereby preventing the thumb, or other fingers, from contacting surface 110, or getting between surface 110 and skin 114. Lastly, referring to FIG. 3A, my cosmetic pad embodiment comprising a thin membrane is gripped by adhesion to the skin of the fingers. In operation thin membrane 104 is urged to adhere to finger 115, prior to rubbing low tension substances from skin 114, or applying new-makeup to skin 114. Membrane 104 may be urged to conform and adhere to finger 115 by stretching thin membrane 104 over finger 115. Alternately, an adhesive may be preapplied to the back side of thin membrane 104 such that pressing of thin membrane 104 to finger 115 will induce conformation and adhesion.

EXAMPLES

FIGS 1, 3A–C, 9A–C

Example 1

A cosmetic pad of the preferred embodiment illustrated in FIG. 1 and FIG. 3B was constructed using a 3 mm (120 mil) thick, 3.8 cm×3.8 cm (1.5"×1.5") section of expanded PTFE gasket tape obtained from W. L. Gore & Associates, Inc (Elkton, Md. 21921), Shore A Hardness was measured as 26. New-makeup was applied and smoothed using my cosmetic pad by applying a small amount of new-makeup to one surface and rubbing it over the skin. It was observed that when compared to cosmetic pad makeup applicators of the prior art my cosmetic pads used approximately 30% to 50% less makeup to cover the human face. Thicker pads were also tested by forming multiple laminations of the 3 mm gasket material using a flexible silicone adhesive. Very good conformability to the contours of the skin was obtained with up to the 4 laminations tested. However, the costs of PTFE compared to the backing materials taught herein will usually preclude the use of all PTFFE pads when a very thick pad is desired.

Example 2

A cosmetic pad of the embodiment illustrated in FIG. 3A was constructed from a 7 cm (2.75") strip of PTFE tape (1.3 cm (0.5") wide PTFE thread sealant tape, distributed by Water Whiz, Inc., Medley, Fla., 33178, Mil. Spec T27730A) ), Shore A Hardness was measured as 70. The strip was placed lengthwise over the index finger, centered on the tip of the finger, and the edges urged to plastically conform around the finger. The strip forms a skin-tight layer over the finger that can then be rubbed over the skin to remove low tension substances. Multiple layers urged onto the finger were tested up to 7 (total thickness about 0.53 mm (21 mil)) with no slipping between layers or formation of creases when rubbed over the skin.

Example 3

A cosmetic pad of the embodiment of the invention shown in FIGS. 3C and 9A–C, was constructed of a layer of PTFE tape (2 cm (0.75") wide PIFE thread seal tape, distributed by Oatey, Cleveland, Ohio, 44135). The tape was conformed over one face of a 2.7 cm (1") diameter, 3.2 mm (⅛") thick polyethylene sponge disc. The tape was secured at the top of the disk by laminating a second 2.7 cm (1") diameter, 3.2 mm (⅛") thick polyethylene sponge disc onto the first using cyanoacrylate glue. Tests employing 5 layers of PTFE showed no loss in crease resistance or flexibility (total thickness approximately 0.4 mm (15 mil)). It is expected that 10 or more layers are possible, if desired.

Example 4

A cosmetic pad of the embodiment of the invention shown in FIGS. 3C and 9A–C, was constructed using the Johnson and Johnson Clear Touch Oil™ Absorbing Sheet material (Shore A hardness of 85) layered over a circular, 2.54 cm (1") diameter, 3.2 mm (⅛") thick polyethylene sponge disc. Since this sheet material is harder and has lower conformability than PTFE membranes, cuts around the circumference of the membrane were helpful to get the edges to lie flat on the top of the sponge. Further, it was much more difficult to get a smooth, form-fitting covering of the edge of the backing. However, although less conformable to the backing, and thus producing a somewhat "baggy" fit to the backing, the formation of creases, with rubbing over the skin, was reduced approximately 10 fold as compared to using these sheets of the prior art alone.

Conclusions, Ramifications, and Scope of Invention

Accordingly, the reader will see that the cosmetic pad of this invention can be rubbed over the skin to preferentially clean the skin of low tension substances such as skin oil and sunscreen residues without the formation of creases in the surface. In addition, my cosmetic pad will not substantially abrade, smudge or otherwise remove previously applied makeup when rubbed over the skin. Moreover, my cosmetic pad may be multiple-use as it can also be used to apply and smooth new-makeup. This is a great advantage over the prior art, as a user is not required to carry or purchase several different pad types to perform daily makeup maintenance. Further, when used to apply new-makeup, significant amounts of makeup is saved as compared to cosmetic pads of the prior art. My cosmetic pad is also very easy to hold and manipulate such that a cosmetologist can easily use them on a client. Removal of excess skin oil significantly reduces the formation of skin blemishes such as darkened keratotic plugs (caused in part by the accumulation of oils that oxidize to a darkened color). In this capacity, my cosmetic pad is effective at preventing the formation of keratotic plugs and can be applied to the skin many times a week (and many times a day if desired) unlike the available keratotic plug removers (U.S. Pat. No. 5,512,277 issued on Apr. 30, 1996, to Uemura et al). My cosmetic pad may also be used to enhance the effectiveness of these keratotic plug removers, by first preparing the skin. Pre-removal of the low surface tension substances on the skin enhances the adhesion of the keratotic plug remover to the keratotic plugs.

While my above description contains many specificities, these should not be construed as limitations on the scope of the invention, but rather as an exemplification of several preferred embodiments thereof. Many other variations are possible. For example, my cosmetic pad can have other shapes, such as triangular or square; the backing can be made of fabric or of polymer materials; the surface or membrane may be colored, or backing darkened, to allow visualization of low tension substance absorption; antibiotic compounds may be added to the membrane or the backing; the membrane may be made of porous PTFE or a material with similar softness, conformability, and surface energy properties, etc.

Accordingly, the scope of the invention should be determined by the appended claims and their legal equivalents, rather than limited to the embodiments and examples given.

I claim:

1. A cosmetic pad for removing low tension substances from skin and for applying and smoothing makeup, comprising:
    (a) a polytetrafluoroethylene having polymeric nodes interconnected by fibrils defining pores, or microporous polypropylene, hydrophobic membrane or sheet, having an equilibrium contact angle with water greater than about 80 degrees,
    (b) said membrane having a shore a hardness less than about 90, a porous surface and a back side,
    (c) said surface having a mean pore size less than about 100 $\mu$m and a substantially low coefficient of friction with said skin, whereby said surface feels smooth to said skin and is nonabrasive to said skin,
    (d) a crease resisting means for substantially inhibiting the formation of creases, which substantially effect the smoothness of said surface when said surface is rubbed over said skin, said crease resisting means having a thickness of said membrane greater than about 0.1 mm and less than about 10 mm, said membrane having a conformability greater than about 4%, whereby said low tension substances may be rapidly, easily, and substantially removed from said skin without substantially removing previously applied makeup,
    (e) said cosmetic pad further includes a flexible backing secured to said membrane by an adhesion means.

2. The cosmetic pad of claim 1, wherein the conformability of said membrane is greater than about 6%.

3. The cosmetic pad of claim 1, wherein said backing is porous and having an equilibrium contact angle with water less than said back side of said hydrophobic membrane, whereby said low tension substances are substantially absorbed from said membrane by said backing.

4. The cosmetic pad of claim 1, further including a handling means disposed on said top side of said backing, whereby said cosmetic pad is easily held and manipulated without touching said surface of said membrane.

5. The cosmetic pad of claim 1, wherein said handling means comprises a collapsible projection, whereby said cosmetic pad can be stored in a more compact form prior to use.

6. A method for improving the health and appearance of skin, comprising providing a cosmetic pad for removing low tension substances from skin and for applying and smoothing makeup, comprising:
    (a) providing a polytetrafluoroethylene having polymeric nodes interconnected by fibrils defining pores, or microporous polypropylene, hydrophobic membrane or sheet, having an equilibrium contact angle with water greater than about 80 degrees,
    (b) said membrane having a shore a hardness less than about 90, a porous surface and a back side,
    (c) said surface having a mean pore size less than about 100 $\mu$m and a substantially low coefficient of friction with said skin, whereby said surface feels smooth to said skin and is nonabrasive to said skin,
    (d) providing a crease resistance means for substantially inhibiting the formation of creases, which substantially effect the smoothness of said surface when said surface is rubbed over said skin,
    (e) said crease resisting means having a thickness of said membrane greater than about 0.1 mm and less than about 10 mm, and said membrane having a conformability greater than about 4%, whereby said low tension substances may be rapidly, easily, and substantially removed from said skin without substantially removing previously applied makeup, and
    (f) applying said surface of said membrane against said skin.

7. The method of claim 6, wherein prior to step (f) new makeup is added to said to skin and distributed over said skin with said surface and whereby said new makeup is not substantially wasted due to absorption into said membrane.

8. The method of claim 6, wherein said thickness of said membrane is less than about 1 mm, and prior to step (f):
    i. said backside of said membrane is contacted against at least one finger, and
    ii. said membrane is urged to conform to said finger, whereby said membrane will substantially adhere to said finger.

9. The method of claim 6, further providing, prior to step (f):
    i. a flexible backing having a face and a top side, and
    ii. layering said back side of said membrane against said face of said backing by a layering means substantially maintaining the porosity of said surface.

10. The method of claim 6, further providing a handle disposed on said top side of said backing.

* * * * *